(12) United States Patent
Martins et al.

(10) Patent No.: US 9,096,618 B1
(45) Date of Patent: Aug. 4, 2015

(54) REGENERATION OF SILYL AND BORYL COMPOUNDS

(71) Applicant: UOP LLC, Des Plaines, IL (US)

(72) Inventors: Susie Martins, Carol Stream, IL (US); Douglas A. Nafis, Mt. Prospect, IL (US); Erin M. Broderick, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/270,008

(22) Filed: May 5, 2014

(51) Int. Cl.
*C07F 7/02* (2006.01)
*C07F 7/08* (2006.01)
*C07F 5/02* (2006.01)

(52) U.S. Cl.
CPC .............. *C07F 7/0801* (2013.01); *C07F 5/027* (2013.01)

(58) Field of Classification Search
USPC .......... 556/7, 9, 474; 585/710, 712, 721, 722, 585/726
See application file for complete search history.

(56) References Cited

U.S. PATENT DOCUMENTS

| | | | |
|---|---|---|---|
| 2,887,500 A | 5/1959 | McEntee | |
| 4,547,595 A | 10/1985 | Chang | |
| 4,824,657 A | 4/1989 | Jadhav | |
| 7,651,970 B2 | 1/2010 | Elomari et al. | |
| 7,674,739 B2 | 3/2010 | Elomari et al. | |
| 7,674,740 B2 | 3/2010 | Harris et al. | |
| 7,678,727 B2 | 3/2010 | Harris et al. | |
| 7,691,771 B2 | 4/2010 | Harris et al. | |
| 7,727,925 B2 | 6/2010 | Elomari et al. | |
| 7,732,363 B2 | 6/2010 | Elomari et al. | |
| 7,732,364 B2 | 6/2010 | Chang et al. | |
| 7,737,067 B2 | 6/2010 | Elomari et al. | |
| 7,737,363 B2 | 6/2010 | Kambe | |
| 7,754,636 B2 | 7/2010 | Elomari et al. | |
| 7,825,055 B2 | 11/2010 | Elomari et al. | |
| 7,884,045 B2 | 2/2011 | Harris et al. | |
| 7,956,002 B2 | 6/2011 | Elomari et al. | |
| 7,995,495 B2 | 8/2011 | Lin | |
| 8,507,396 B2 | 8/2013 | Elomari et al. | |
| 8,524,623 B2 | 9/2013 | Timken et al. | |
| 2007/0142211 A1 | 6/2007 | Elomari et al. | |
| 2007/0142213 A1 | 6/2007 | Elomari et al. | |
| 2007/0142215 A1* | 6/2007 | Harris et al. | 502/53 |
| 2007/0142216 A1 | 6/2007 | Harris et al. | |
| 2007/0142217 A1 | 6/2007 | Elomari et al. | |
| 2007/0142218 A1 | 6/2007 | Harris et al. | |
| 2007/0249485 A1 | 10/2007 | Elomari et al. | |
| 2007/0249486 A1 | 10/2007 | Elomari et al. | |
| 2010/0130804 A1 | 5/2010 | Timken et al. | |
| 2010/0147740 A1 | 6/2010 | Elomari et al. | |
| 2012/0283500 A1 | 11/2012 | Liu et al. | |

FOREIGN PATENT DOCUMENTS

| | | |
|---|---|---|
| CN | 102666444 A | 9/2012 |
| JP | 55001870 | 1/1980 |

OTHER PUBLICATIONS

Schmidt et al., "Disproportionation of Light Paraffins," Energy & Fuels (2008), vol. 22, 1812-1823.

Iranpoor et al. "Diphenylphosphinite ionic liquid (IL-OPPh2): A solvent and ligand for palladium . . . "Journal of Organometallic Chemistry(2010), 695(6), 887-890.

Gevorgyan et al. "Reduction of Alkoxysilanes, Halo-silanes and -Germanes with Lithium . . . " Journal of Organometallic Chemistry (1985), vol. 284, C31-C32.

* cited by examiner

*Primary Examiner* — Sudhakar Katakam
*Assistant Examiner* — Pancham Bakshi (57) ABSTRACT

A method of regenerating a silyl or boryl compound is described. The silyl or boryl compound is contained in an organic phase with conjunct polymer. The silyl or boryl compound is chemically reduced with a hydrogen containing compound in a silane or borane regeneration zone under regeneration conditions to form at least one regenerated silane or borane compound and a metal salt compound. The regenerated silane or borane compound is recovered.

12 Claims, 3 Drawing Sheets

REGENERATION OF SILYL AND BORYL COMPOUNDS

BACKGROUND OF THE INVENTION

Commercially, the alkylation of isoparaffins is catalyzed by acids such as sulfuric acid and hydrofluoric acid. Conjunct polymer (acid soluble oils, (ASO) also known as red oil) forms as a byproduct of the alkylation reaction, as well as other hydrocarbon reactions. When too much conjunct polymer is present, the acid catalyst loses its effectiveness. The acid must be replaced with stronger acid, or the conjunct polymer must be removed in order to reactivate the catalyst. With sulfuric acid as the catalyst, the ASO is burned, and with hydrofluoric acid, the hydrofluoric acid is distilled away from the ASO. Sulfuric acid and hydrofluoric acid are hazardous and corrosive, and their use in industrial processes requires a variety of environmental controls.

There has been a move to replace the use of sulfuric acid and hydrofluoric acid with more environmentally friendly materials.

One such process utilizes acidic ionic liquids as catalysts in hydrocarbon conversion processes, such as alkylation, isomerization, disproportionation, reverse disproportionation, and oligomerization. Conjunct polymers are byproducts of the hydrocarbon reaction using ionic liquids, and they form a complex with the ionic liquid catalyst. The ionic liquid catalyst loses its effectiveness over time as the amount of conjunct polymer increases. It must then either be replaced or regenerated. Because ionic liquids are typically fairly expensive, processes for regenerating the ionic liquid catalysts are needed.

A variety of methods for regenerating ionic liquids have been developed. The ionic liquid containing the conjunct polymer could be contacted with a reducing metal (e.g., Al), an inert hydrocarbon (e.g., hexane), and hydrogen and heated to about 100° C. The conjunct polymer will be transferred to the hydrocarbon phase, allowing for the conjunct polymer to be removed from the ionic liquid phase. See e.g., U.S. Pat. No. 7,651,970; U.S. Pat. No. 7,825,055; U.S. Pat. No. 7,956,002; and U.S. Pat. No. 7,732,363.

Another method involves contacting the ionic liquid containing the conjunct polymer with a reducing metal (e.g., Al) in the presence of an inert hydrocarbon (e.g. hexane), but in the absence of added hydrogen, and heating to about 100° C. The conjunct polymer will be transferred to the hydrocarbon phase, allowing for the conjunct polymer to be removed from the ionic liquid phase. See e.g., U.S. Pat. No. 7,674,739.

Still another method of regenerating the ionic liquid involves contacting the ionic liquid containing the conjunct polymer with a reducing metal (e.g., Al), HCl, and an inert hydrocarbon (e.g. hexane), and heating to about 100° C. The conjunct polymer will be transferred to the hydrocarbon phase, allowing for the CP to be removed from the IL phase. See e.g., U.S. Pat. No. 7,727,925.

The ionic liquid can be regenerated by adding a homogeneous metal hydrogenation catalyst (e.g., $(PPh_3)_3RhCl$) to the ionic liquid containing the conjunct polymer and an inert hydrocarbon (e.g. hexane). Hydrogen would be introduced, and the conjunct polymer would be reduced and transferred to the hydrocarbon layer. See e.g., U.S. Pat. No. 7,678,727.

Another method for regenerating the ionic liquid involves adding HCl, isobutane, and an inert hydrocarbon to the ionic liquid containing the conjunct polymer and heating to about 100° C. The conjunct polymer would react to form an uncharged complex, which would transfer to the hydrocarbon phase. See e.g., U.S. Pat. No. 7,674,740.

The ionic liquid could also be regenerated by adding a supported metal hydrogenation catalyst (e.g. Pd/C) to the ionic liquid containing the conjunct polymer and an inert hydrocarbon (e.g. hexane). Hydrogen would be introduced and the conjunct polymer would be reduced and transferred to the hydrocarbon layer. See e.g., U.S. Pat. No. 7,691,771.

Still another method involves adding a basic reagent that displaces the conjunct polymer and is a part of the regeneration of the catalyst. The basic reagents are described as nitrogen-containing compounds such as amines, pyridinium compounds, or pyrrolidinium compounds. For example, a suitable substrate (e.g. pyridine) is added to the ionic liquid containing the conjunct polymer. After a period of time, an inert hydrocarbon would be added to wash away the liberated conjunct polymer. The ionic liquid precursor [butylpyridinium][Cl] would be added to the ionic liquid (e.g. [butylpyridinium][$Al_2Cl_7$]) containing the conjunct polymer followed by an inert hydrocarbon. After a given time of mixing, the hydrocarbon layer would be separated, resulting in a regenerated ionic liquid. The solid residue would be converted to catalytically active ionic liquid by adding $AlCl_3$. See e.g., U.S. Pat. No. 7,737,363 and U.S. Pat. No. 7,737,067.

Another method involves adding the ionic liquid containing the conjunct polymer to a suitable substrate (e.g. pyridine) and an electrochemical cell containing two aluminum electrodes and an inert hydrocarbon. A voltage would be applied and the current measured to determine the extent of reduction. After a given time, the inert hydrocarbon would be separated, resulting in a regenerated ionic liquid. See, e.g., U.S. Pat. No. 8,524,623.

All of these regeneration approaches have drawbacks. Many of them cannot achieve above 90% conversion of the conjunct polymer, which then builds up in the process. Of those that can provide high levels of conversion, hydrogenation of the spent ionic liquid with supported (e.g., U.S. Pat. No. 7,691,771) and unsupported (e.g., U.S. Pat. No. 7,678,727) hydroprocessing catalysts may result in the active catalytic metals being extracted into the ionic liquid phase. Many catalyst supports also react irreversibly with the chloroaluminate anion of the ionic liquid. Although the use of metallic aluminum for regeneration (e.g., U.S. Pat. No. 7,995,495) is effective, it introduces undesirable solids handling issues into the refinery. Finely divided aluminum is pyrophoric and presents safety issues in a refining environment. This approach also results in the creation of additional $AlCl_3$, which has to be removed from the ionic liquid phase (e.g., U.S. Pat. No. 7,754,636) to avoid building up to a molar ratio relative to the ionic liquid cation at which solids will start precipitating out of solution and cause plugging issues. Electrochemical approaches (e.g., U.S. Pat. No. 8,524,623) are not economically viable at commercial scales.

Therefore, there remains a need for additional methods of regenerating ionic liquids used as catalysts in reactions.

SUMMARY OF THE INVENTION

One aspect of the invention involves a method for regenerating at least one silyl or boryl compound. In one embodiment, the method includes providing an organic phase comprising conjunct polymer and the at least one silyl or boryl compound. The at least one silyl or boryl compound is chemically reduced with a hydrogen containing compound in a silane or borane regeneration zone under regeneration conditions to form at least one regenerated silane or borane compound and a metal salt compound. The at least one regenerated silane or borane compound is recovered.

Another aspect of the invention is a method for regenerating deactivated acidic catalyst containing conjunct polymer. In one embodiment, the method includes contacting a deactivated acidic catalyst containing the conjunct polymer with at least one silane or borane compound in a catalyst regeneration zone under regeneration conditions, the acidic catalyst selected from the group consisting of sulfuric acid, hydrofluoric acid, trifluoromethanesulfonic acid, phosphoric acid, boron trifluoride, and acidic ionic liquids, the conjunct polymer reacting with the at least one silane or borane compound resulting in a catalyst phase and an organic phase containing the conjunct polymer and at least one silyl or boryl compound. The at least one silyl or boryl compound is chemically reduced with a metal hydride in a silane or borane regeneration zone under regeneration conditions to form at least one regenerated silane or borane compound and a metal salt compound. The at least one regenerated silane or borane compound is recovered.

DETAILED DESCRIPTION OF THE INVENTION

It has been discovered that deactivated acidic catalysts containing conjunct polymer can be regenerated using a reagent that contains no metals and that reacts at mild conditions. In some embodiments, the reagent can be easily separated by gravity from the ionic liquid. When a liquid reagent is used, the process does not produce any net solids that have to be handled or treated. When solvents are used with liquid reagent, the liquid reagent can be easily separated from the solvent. In addition, the mild conditions under which the process can be performed may result in lower operating costs than processes requiring harsher conditions. The mild operating conditions may also result in lower capital costs due to the ability to use less expensive materials of construction.

By deactivated acidic catalysts containing conjunct polymer, we mean acidic catalysts that have been used in hydrocarbon conversion processes, and in which conjunct polymers have formed. Acidic catalysts which form conjunct polymers in hydrocarbon conversion processes include sulfuric acid, hydrofluoric acid, trifluoromethanesulfonic acid (triflic acid), phosphoric acid, boron trifluoride, and acidic ionic liquids. By conjunct polymer, we mean the olefinic, conjugated cyclic hydrocarbons that form as a byproduct of various hydrocarbon conversion processes, including but not limited to alkylation, oligomerization, isomerization, disproportionation, and reverse disproportionation.

By acidic ionic liquid, we mean an ionic liquid capable of catalyzing reactions typically carried out with an acid. As known in the art, acids such as sulfuric acid and hydrofluoric acid are often used to catalyze these reactions. These reactions include, e.g. alkylation, oligomerization, isomerization, disproportionation, and reverse disproportionation. Oftentimes the acids employed in these reactions have Hammett acidity functions ($H_0$) less than 7, or less than 5, or less than 3, or less than 0, or less than −3, or less than −5, or less than −7, or less than −9. If the ionic liquid does not possess an acidic proton in its structure (e.g. 1-butyl-3-methylimidazolium heptachloroaluminate), addition of an exogenous acid is acceptable, provided the Hammett acidity function ($H_0$) of the added acid is less than 7 within the ionic liquid, or less than 5, or less than 3, or less than 0, or less than −3, or less than −5, or less than −7, or less than −9. Acidic chloroaluminate-containing ionic liquids have a molar ratio of Al to cation greater than 1.

By the term about, we mean within 10% of the specified value, or within 5%, or within 1%.

The contact of a silane or borane compound with an acidic catalyst that contains conjunct polymer releases the conjunct polymer from the acidic catalyst. When the acidic catalyst is an ionic liquid, the ionic liquid can then be reactivated with acid. Other acidic catalysts may also require reactivation. The conjunct polymer can be separated from the silane or borane compound, and the silane or borane compound can be recycled.

The silane or borane reacts with the acid sites of the acidic catalyst. For example, the silane or borane will react with the acidic sites in a halometallate ionic liquid to form a silyl or boryl halide. The acid sites that were binding the conjunct polymer are no longer present, which allows the conjunct polymer to be removed.

The deactivated acidic catalyst and the silane or borane compound are contacted for a period of time sufficient to allow the conjunct polymer to react with the silane or borane compound. For silane compounds, this will typically take in the range of about 5 sec to about 1 hr, or about 1 min to about 45 min, or about 1 min to about 30 min, or about 1 min to about 15 min. For borane compounds at room temperature, the reaction is slower than with the silane, e.g., many hours. The time is less at elevated temperatures, e.g., less than 2 hr at 60° C.

The contacting typically takes place at a temperature in the range of from about −20° C. to the degradation temperature of the acidic catalyst. For ionic liquids, the upper limit is the decomposition temperature of the ionic liquid. A typical temperature range is about 20° C. to about 80° C. In some embodiments, the contacting takes place at room temperature. In some embodiments with borane compounds, the contacting takes place at temperatures in the range of about 40° C. to about 80° C., or about 70° C.

The pressure is typically ambient pressure, although higher or lower pressures could be used if desired.

In some embodiments, the reaction is conducted under an inert gas so that hydrolysis of the silane or borane does not occur. When the acidic catalyst is an ionic liquid, the ionic liquid may also hydrolyze, so these reactions are desirably conducted under an inert gas. Suitable inert gases include, but are not limited to, nitrogen, helium, neon, argon, krypton, and xenon.

In some embodiments, the volume ratio of the solvent to the deactivated acidic ionic liquid is in a range of about 0.25:1 to about 10:1.

In some embodiments, the molar ratio of the silane compound to the conjunct polymer is in a range of about 1:1 to about 5:1, or about 2:1 to about 3:1. In some embodiments, the molar ratio of the borane compound to the conjunct polymer is in a range of about 0.5:1 to about 5:1, or about 2:1 to about 3:1. In some embodiments, the silane or borane compound can be present in excess of the amount needed for reaction with the conjunct polymer, and the excess silane or borane compound can act as a solvent. In these cases, the molar ratio of the silane compound or borane compound to the conjunct polymer is more than 5:1, e.g., in the range of 10:1 to about 1000:1.

The contacting can take place in any suitable process, such as solvent extraction, or contacting in one or more mixer/settlers.

The reaction will proceed simply by contacting the silane or borane compound with the liquid acidic catalyst. However, the mixture can be stirred to increase the contact between the silane or borane compound and the acidic catalyst. Stirring is particularly useful when the acidic catalyst is an ionic liquid.

The contacting step may be practiced in laboratory scale experiments through full scale commercial operations. The process may be operated in batch, continuous, or semi-continuous mode. The contacting step can take place in various ways, with both countercurrent and co-current flow processes being suitable. The order of addition of the reactants is not critical. For example, the reactants can be added individually, or some reactants may be combined or mixed before being combined or mixed with other reactants.

After contacting the acidic catalyst and the silane or borane compound, two phases result, a catalyst phase containing the acidic catalyst and an organic phase containing the conjunct polymer and the silyl or boryl compound and solvent, if present. In some embodiments, the phases will separate due to the density difference between the two phases. In other embodiments, other separation processes may be needed. In some embodiments, the conjunct polymer can be decanted away. Decanting can be suitable if there is enough conjunct polymer present and it separates from the acidic catalyst.

When the acidic catalyst is an ionic liquid, the ionic liquid can be reactivated by adding an appropriate acid. The reactivated acidic catalyst can then be recycled to the hydrocarbon conversion process. Other acidic catalysts may also need to be reactivated by adding an appropriate acid.

The organic phase containing the conjunct polymer and the silyl or boryl compound can be treated as well. The conjunct polymer can be separated from the silyl or boryl compound, and the silyl or boryl compound can be regenerated. The regenerated silane or borane can be recycled and reused to contact with the deactivated acidic catalyst.

The silyl or boryl compound can be chemically reduced to regenerate the silane or borane compound. One method of regeneration is reaction with one or more compounds containing hydrogen, such as one or more metal hydrides. The reaction can take place in a suitable solvent, such as tetrahydrofuran (THF) or toluene. The silyl or boryl compound is converted back to the silane or borane compound and a metal salt byproduct. Suitable metal hydrides include, but are not limited to, LiH, NaH, $CaH_2$, $NaAlH_4$, $LiAlH_4$, KH, $NaBH_4$, diisobutylaluminum hydride, and the like.

The silane or borane regeneration reaction can take place in a few hours at temperatures in the range of about 25° C. to about 70° C., depending on the metal hydride and solvent used.

When the silane or borane compound is mixed with a solvent for the contacting step, the solvent can be recovered before or after separating the conjunct polymer from the silyl or boryl compound. The recovered solvent can be recycled and reused in the process.

In some embodiments, the conjunct polymer is separated from the solvent and silyl or boryl compound at the same time. The separation can take place in a fractionation column, for example. The conjunct polymer may also be adsorbed onto a solid adsorbent such as alumina or activated carbon, and later removed by combustion for heat recovery.

Alternatively, if the solvent is compatible with the subsequent reaction regenerating the silane or borane, the solvent may not be removed. In those situations, the conjunct polymer is separated from the solvent and silyl or boryl compound mixture, and the silyl or boryl compound is regenerated while in the solvent. The solvent and regenerated silane or borane can then be recycled and reused.

In some embodiments, the separation of the conjunct polymer from the silyl or boryl compound may not be complete because the silyl or boryl compound may co-boil with the lower molecular weight conjunct polymer making complete removal difficult.

The regenerated silane or borane can be separated from the metal salt byproduct and recycled back for use in the process. Suitable separation processes include, but are not limited to, filtration and decantation.

In another embodiment, the acidic catalyst containing conjunct polymer is passed through a resin containing silane or borane moieties. Suitable resins include, but are not limited to, polystyrene and polyester. The silane or borane moieties react with the acid sites, and the conjunct polymer can be extracted into an organic phase. The ionic liquid is reactivated by adding acid.

In one embodiment, the regeneration process is a solvent extraction process. For ease of discussion, the use of deactivated acidic ionic liquid in the solvent extraction process will be described. However, as will be understood by those of skill in the art, other acidic catalysts which form conjunct polymers could also be used.

In the solvent extraction method, a solvent and a silane or borane compound are added to the ionic liquid containing conjunct polymer. The solvent and the silane or borane compound can be pre-mixed and added together, or they can be added separately, either at the same time or sequentially. Solvent is not always necessary, but it will maximize recovery, removal, and separation of the conjunct polymer.

The silane or borane compound reacts with the free acid and acid sites associated with the conjunct polymer. After these acid sites are quenched, the conjunct polymer migrates from the ionic liquid phase to the organic phase and can be extracted.

In a system without stirring or after stirring is ended, the components can separate into two phases based on the density difference between the ionic liquid phase and the organic phase which contains the conjunct polymer. The ionic liquid will settle to the bottom, and the silane or borane and conjunct polymer will be on top of the ionic liquid layer. Increasing the top layer with additional solvent will increase conjunct polymer recovery.

The deactivated ionic liquid, the solvent, and the silane or borane compound are contacted long enough for the conjunct polymer to react with the silane or borane compound, typically about 5 sec to about 1 hr. The deactivated ionic liquid, the solvent, and the silane or borane compound are typically mixed while being contacted.

The deactivated ionic liquid, the solvent, and the silane or borane compound are typically contacted at a temperature in the range of from about −20° C. to less than the decomposition temperature of the ionic liquid, or about 20° C. to about 80° C. In some embodiments, the contacting takes place at room temperature.

The mixture is then allowed to separate into two phases: an ionic liquid phase and a hydrocarbon phase. In some embodiments, separation occurs due to the density difference between the ionic liquid phase and the hydrocarbon phase. Separation typically takes on the order of a few minutes to hours; it is generally less than about 1 hr.

The solvent layer is decanted from the ionic liquid. The ionic liquid can be further washed with solvent (either the same solvent used in the extraction or a different one), if desired. As the reaction occurs, the conjunct polymer is extracted into the solvent layer. Volatiles are removed from the organic layer to isolate the conjunct polymer as a viscous oil. In one embodiment, the volatiles can be removed by heating the material under reduced pressure.

In some embodiments, the addition of an acid or an acid precursor reactivates the ionic liquid following removal of the conjunct polymer. Suitable acids and acid precursors include, but are not limited to, HCl, tert-butyl chloride, or 2-chlorobutane. The acid precursor can be any molecule that will break down to form the acid. Reactivation of the ionic liquid with acid or acid precursor typically takes about 5 sec to about 30 min. It can be done at a range of temperatures. For convenience, it is typically done at the same conditions as the hydrocarbon conversion process which generates the conjunct polymer.

The ionic liquid containing the conjunct polymer can be pre-treated before it is contacted with the silane or borane compound. The pretreatment can be used to remove any free acid, such as HCl, which might increase the consumption of the silane or borane compound, and/or any dissolved solvent, which might associate with the conjunct polymer. The pretreatment can be in a fractionation column, for example.

The ionic liquid can be any acidic ionic liquid. There can be one or more ionic liquids. The ionic liquid comprises an organic cation and an anion. Suitable cations include, but are not limited to, nitrogen-containing cations and phosphorus-containing cations. Suitable organic cations include, but are not limited to:

where $R^1$-$R^{21}$ are independently selected from $C_1$-$C_{20}$ hydrocarbons, $C_1$-$C_{20}$ hydrocarbon derivatives, halogens, and H. Suitable hydrocarbons and hydrocarbon derivatives include saturated and unsaturated hydrocarbons, halogen substituted and partially substituted hydrocarbons and mixtures thereof. $C_1$-$C_8$ hydrocarbons are particularly suitable.

The anion can be derived from halides, typically halometallates, and combinations thereof. The anion is typically derived from metal and nonmetal halides, such as metal and nonmetal chlorides, bromides, iodides, fluorides, or combinations thereof.

Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br^-$). In some embodiments, the metal is aluminum, with the mole fraction of aluminum ranging from 0<Al<0.25 in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF_4^-$.

The silane compound can be any compound with a reactive SiH moiety. In some embodiments, the silane compound is an organosilane. There can be one or more silanes. Suitable silane compounds include, but are not limited to, silanes having the formulas: $R_3SiH$, $R_2SiH_2$, $RSiH_3$, or $SiH_4$ where each R is independently selected from hydrocarbons or halides. Examples of suitable silanes include triethylsilane, trimethylsilane, triisopropylsilane, and the like. In some embodiments, the silane can be a silane-containing resin.

The silyl compound will be the reaction product of the silane compound and the acid site ($H^+$) on the conjunct polymer. When the silane has one of the formulas above, the silyl compound will have the formula: $R_3SiX$, $R_2SiX_2$, $RSiX_3$, or $SiX_4$, where each R is independently selected from hydrocarbons, and each X is independently selected from halides.

The borane compound can be any borane compound having a reactive B—H bond. In some embodiments, the borane compound is an organoborane. There can be one or more boranes. Suitable borane compounds include, but are not limited to, boranes having the formulas: $R_2BH$ or where each R is independently selected from hydrocarbons or halides, or $B_2H_6$, or combinations thereof. Examples of suitable boranes include 9-borabicyclo(3,3,1)nonane, trimesitylborane, trisec-butylborane, diborane, and the like. In some embodiments, the borane can be a borane-containing resin.

The boryl compound will be the reaction product of the borane compound and the acid site ($H^+$) on the conjunct polymer. When the borane has the formula $R_2BH$, the boryl compound will have the formula: $R_2BX$, where each R is independently selected from hydrocarbons or halides. When the borane has the formula $B_2H_6$, the boryl compound is a boron halide compound.

The solvent will depend on the acidic catalyst being regenerated. The solvent can be any solvent which is capable of forming a separate phase from the catalyst phase. There can be one or more solvents. Suitable solvents for halometallate ionic liquids include, but are not limited to, n-paraffins, iso-paraffins, and cyclic paraffins, such as $C_4$ to $C_{10}$ paraffins, and aromatic solvents. If the ionic liquid is soluble in hydrocarbons, more polar solvents which are not miscible in the ionic liquid would be used. The use of organic solvents may be less desirable with oxidizing acids.

Figure 1:
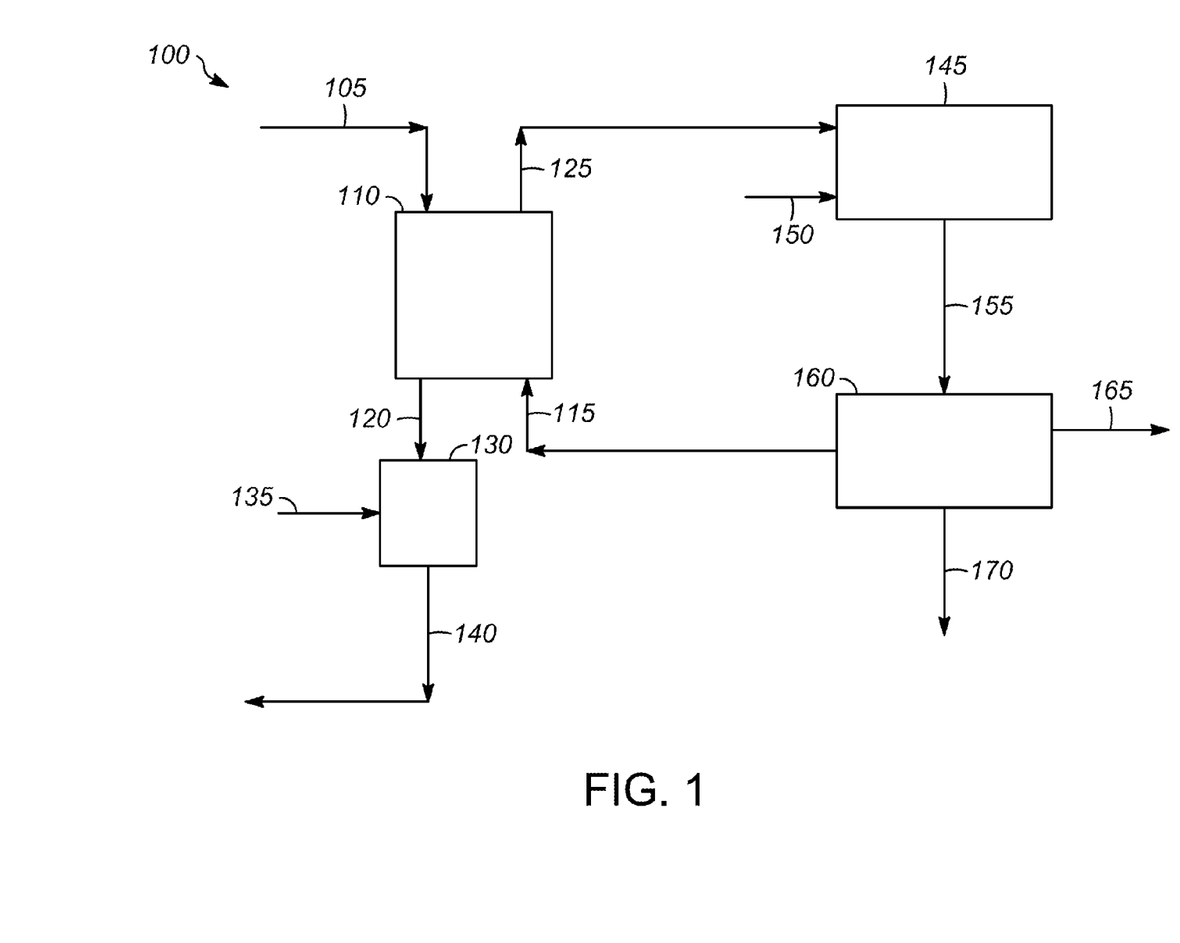
FIG. 1 illustrates one embodiment of a method for regenerating deactivated acidic ionic liquid catalyst containing conjunct polymer according to the present invention.

FIG. 1 illustrates one embodiment of the process 100. For ease of discussion, the process will be described using tributylhexylphosphonium chloroaluminate ionic liquid (TBHP-$Al_2Cl_7$), triethylsilane (TESi-H), and n-butane ($nC_4$) solvent. Other acidic catalysts, (including other acidic ionic liquids), silane compounds, borane compounds, and solvents could also be used, as would be understood by those skilled in the art.

The deactivated ionic liquid feed 105 is introduced into a reactive extraction zone 110. The ionic liquid is TBHP-$Al_2Cl_7$. The deactivated ionic liquid feed 105 contains where [$CPH^+$] represents the protonated conjunct polymer.

A solvent/silane compound stream 115 is introduced into the reactive extraction zone 110 and flows countercurrent to the deactivated ionic liquid feed 105. The solvent/silane compound stream 115 contains The deactivated ionic liquid feed 105 reacts with the TESi-H to form triethylsilylchloride (TESi-Cl). Although not wishing to be bound by theory, it is believed that a reaction occurs between the TESi-H and the acid sites tied up with the conjunct polymers. When the conjunct polymer is no longer protonated, it becomes an organic-like molecule (no longer charged), so it is easily transferred to the organic phase.

The ionic liquid phase with the conjunct polymer removed 120 can be separated from the hydrocarbon phase by taking advantage of the fact that it has a higher density than the hydrocarbon phase 125.

The ionic liquid phase 120 contains dissolved/suspended AlCl$_3$, which is reactivated by adding an acid 135, such as HCl, in Zone 130 to restore the active acid sites:

[AlCl$_3$]+HCl→[H$^+$][AlCl$_4^-$].

The re-activated ionic liquid 140 contains

[TBHP$^+$][AlCl$_4^-$/AlCl$_3$]+[H$^+$][AlCl$_4^-$].

The re-activated ionic liquid 140 can then be recycled back to the hydrocarbon conversion process.

The hydrocarbon phase 125 contains the TESi-Cl, solvent, conjunct polymer, hydrogen, and any unreacted TESi-H.

[TESi-Cl]+[nC$_4$]+[CP]+[H$_2$]+[TESi-H].

The TESi-Cl in the hydrocarbon phase 125 is reacted to regenerate the TESi-H in a reaction zone 145. One method of reacting the TESi-Cl is with reducing agents that contain H$^-$, such as metal hydrides 150.

[TESi-Cl]+MH→[TESi-H]+[MCl].

The effluent 155 from the reaction zone 145 contains the regenerated TESi-H, the solvent, the conjunct polymer, and the metal salt.

[TESi-H]+[nC$_4$]+[CP]+[MCl].

The effluent 155 from the reaction zone 145 can be sent to a separation zone 160 where the solvent and TESi-H are separated from the metal salt 165 and conjunct polymer 170. The solvent and TESi-H can be recycled to the extraction zone 110 as stream 115.

Figure 2:
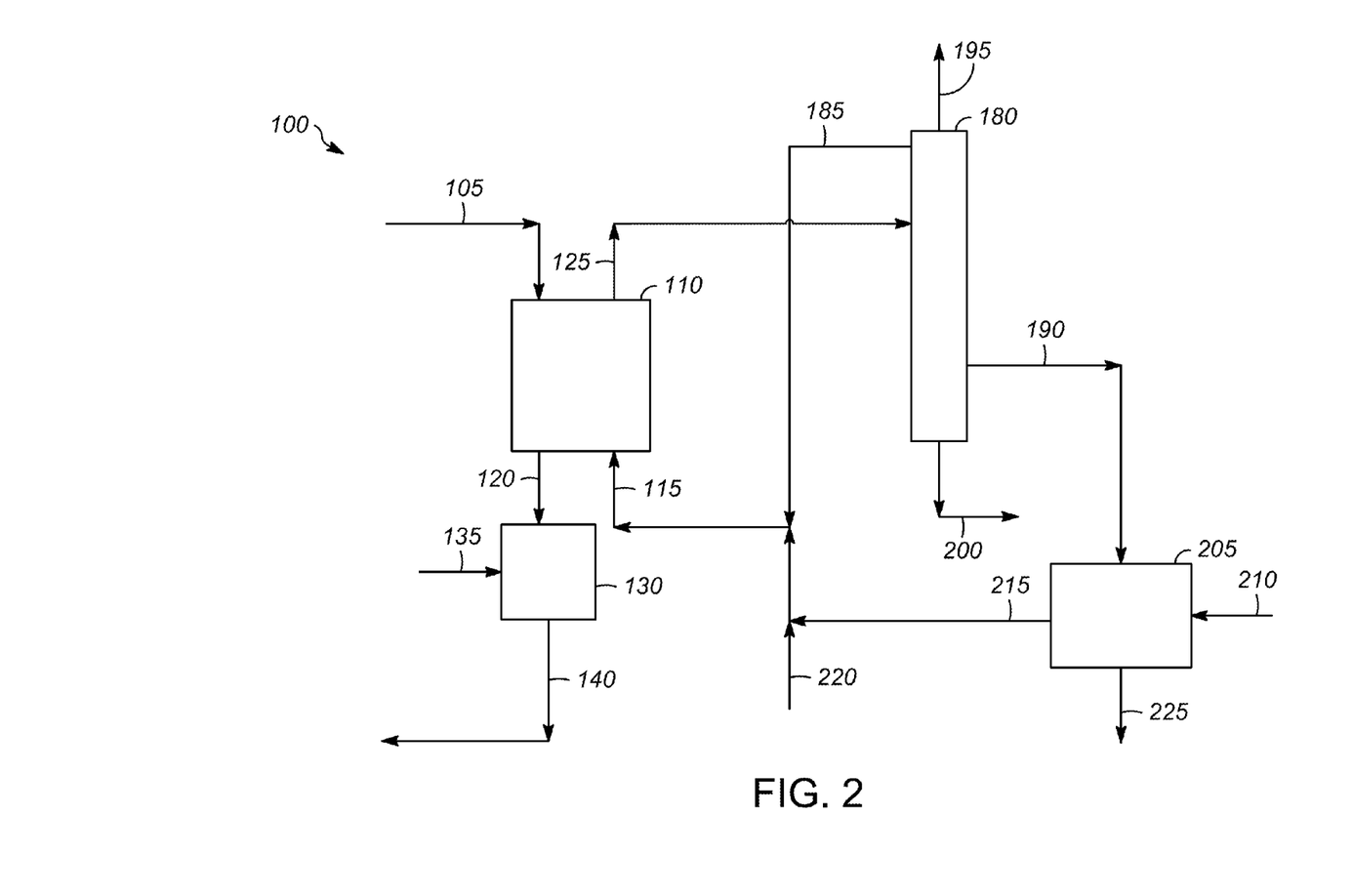
FIG. 2 illustrates another embodiment of a method for regenerating deactivated acidic ionic liquid catalyst containing conjunct polymer according to the present invention.

FIG. 2 illustrates another embodiment of the treatment of the hydrocarbon phase 125. As described above, the hydrocarbon phase 125 contains the TESi-Cl, solvent, and conjunct polymer, hydrogen, and any unreacted TESi-H. In this embodiment, the hydrocarbon phase 125 is sent to a separation zone 180 where the solvent and any unreacted TESi-H 185 are removed and recycled to the reactive extraction zone 110. Side stream 190 contains the TESi-Cl. Overhead stream 195 may contain hydrogen, which can be recovered. Bottoms stream 200 contains the conjunct polymer, which can be recovered for blending into a suitable refinery stream. Stream 190 is sent to reaction zone 205 where the silyl compound is regenerated. A metal hydride 210 is added to reaction zone 205 to convert the TESi-Cl to TESi-H and byproduct metal chloride. The TESi-H stream 215 can be combined with recycled solvent 185 and make-up solvent and/or TESi-H 220 and recycled to the reactive extraction zone 110. The metal chloride 225 is removed.

EXAMPLES

Preparation of Spent Ionic Liquid

The spent ionic liquid samples were generated in a continuous alkylation process in which 2-butenes were contacted with tributylhexylphosphonium heptachloroaluminate ionic liquid in the presence of isobutane and 2-chlorobutane. Contacting took place in a stirred 300 mL autoclave stirred at 1200 rpm. The mixture was continuously transferred to a gravity separator and the IL recycled to the alkylation reactor. Flow rates and feed ratios varied over the course of the reaction which took place over several days to weeks for the various samples. At the end of each run, the heavy fraction containing ionic liquid was collected and stored under nitrogen. The % CP in each of the spent samples was determined by extraction and isolation of CP. The spent ionic liquid was mixed with water. The CP was extracted from the IL/water mixture with hexane. The hexane was removed on a rotary evaporator and the mass of the isolated CP was determined.

Examples 1-6

Under a nitrogen atmosphere, 4 g of spent TBHP-Al$_2$Cl$_7$ IL containing 10.42% wt conjunct polymer was added to a glass vial equipped with a stir bar, followed by the required amount of anhydrous nC$_8$ to obtain a 0.86 vol ratio of nC$_8$ to IL. The amount of triethylsilane was varied, as shown in Table 1. Stirring was initiated and continued for 15 minutes at room temperature. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The extent of CP removal ranged from 60-95% wt. Increasing the triethylsilane to CP mol ratio improved the extent of CP removal. The results are shown in Table 1.

TABLE 1

Impact of TES:CP mol ratio on % CP Removal.
Experiments conducted with 4 g of spent IL, at 0.86
volume ratio of nC$_8$ to IL, 25° C., for 15 minutes.

| Experiment | % CP in IL | TES:CP mol ratio added | % CP Removed | TESi: CP mol ratio converted |
|---|---|---|---|---|
| Example 1 | 10.42% | 1.63 | 66% | 1.63 |
| Example 2 | | 1.83 | 60% | 1.80 |
| Example 3 | | 2.01 | 74% | 2.01 |
| Example 4 | | 2.49 | 95% | 2.44 |
| Example 5 | | 2.71 | 85% | 2.49 |
| Example 6 | | 2.90 | 86% | 2.60 |

Example 7

Under a nitrogen atmosphere, 50 g of spent TBHP-Al$_2$Cl$_7$ IL containing 10.99% wt conjunct polymer was added to a flask equipped with a stir bar, followed by the required amount of anhydrous nC$_6$ to obtain the indicated solvent to IL ratio. The appropriate amount of triethylsilane was added to obtain the indicated ratio of triethylsilane to conjunct polymer. Stirring was initiated and continued for 15 minutes at room temperature. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The extent of CP removal was determined to be 68% wt. The results are shown in Table 2.

Example 8

Under a nitrogen atmosphere, 4 g of spent TBHP-Al$_2$C$_7$ IL containing 10.42% wt conjunct polymer was added to a glass vial equipped with a stir bar, followed by the required amount of anhydrous nC$_8$. The appropriate amount of triethylsilane was added. Stirring was initiated and continued for 15 minutes at room temperature. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The % wt CP removal was determined to be 74%. The results are shown in Table 2.

TABLE 2

Impact of hydrocarbon type on % CP Removal. Experiments conducted at 25° C., for 15 minutes.

| Experiment | % CP in IL | TES:CP mol ratio added | g IL | Solvent | Solvent:IL vol ratio | % CP Removed | TESi:CP mol ratio converted |
|---|---|---|---|---|---|---|---|
| Example 7 | 10.99% | 2.13 | 50 | nC6 | 0.39 | 68% | 2.13 |
| Example 8 | 10.42% | 2.01 | 4 | nC8 | 0.55 | 74% | 2.01 |

Examples 9-10

Under a nitrogen atmosphere, 16 g of spent TBHP-Al$_2$Cl$_7$ IL containing 3.04% wt conjunct polymer was added to a flask equipped with a stir bar, followed by the required amount of anhydrous nC$_8$ to obtain the indicated solvent to IL ratio, which was varied as shown in Table 3. The appropriate amount of triethylsilane was added to obtain the indicated ratio of triethylsilane to conjunct polymer. Stirring was initiated and continued for 15 minutes at room temperature. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The % wt CP removal was determined to be 64% and 90%, respectively. The results are shown in Table 3.

Examples 11-12

Under a nitrogen atmosphere, 14 g of spent TBHP-Al$_2$Cl$_7$ IL containing 6.82% wt conjunct polymer was added to a flask equipped with a stir bar, followed by the required amount of anhydrous nC$_8$, which was varied as shown in Table 3. The appropriate amount of triethylsilane was added. Stirring was initiated and continued for 15 minutes at room temperature. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The % wt CP removal was determined to be 81% and 72%, respectively. The results are shown in Table 3.

Examples 13-16

Under a nitrogen atmosphere, 4 g of spent TBHP-Al$_2$Cl$_7$ IL containing 10.42% wt conjunct polymer was added to a glass vial equipped with a stir bar, followed by the required amount of anhydrous nC$_8$, which was varied as shown in Table 3. The appropriate amount of triethylsilane was added. Stirring was initiated and continued for 15 minutes at room temperature. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The % wt CP removal ranged from 74% to 78%. The results are shown in Table 3.

Examples 17-18

Under a nitrogen atmosphere, 4 g of spent TBHP IL containing 14.80% wt conjunct polymer was added to a glass vial equipped with a stir bar, followed by the required amount of anhydrous nC$_8$, which was varied as shown in Table 3. The appropriate amount of triethylsilane was added. Stirring was initiated and continued for 15 minutes at room temperature. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The % wt CP removal was determined to be 67% and 76%, respectively. The results are shown in Table 3.

TABLE 3

Impact of hydrocarbon to IL volume ratio on % CP Removal. Experiments conducted in nC$_8$ at 25° C., for 15 minutes.

| Experiment | % CP in IL | TES:CP mol ratio added | g IL | Solvent: IL vol ratio | % CP Removed | TESi:CP mol ratio converted |
|---|---|---|---|---|---|---|
| Example 9 | 3.04% | 2.27 | 16.0 | 0.85 | 64% | 2.26 |
| Example 10 | | | | 1.18 | 90% | 2.24 |
| Example 11 | 6.82% | 2.28 | 14.0 | 0.86 | 81% | 2.28 |
| Example 12 | | | | 1.51 | 72% | 2.20 |
| Example 13 | 10.42% | 2.01 | 4.0 | 0.55 | 74% | 2.01 |
| Example 14 | | | | 0.65 | 77% | 2.00 |
| Example 15 | | | | 0.75 | 78% | 2.01 |
| Example 16 | | | | 0.86 | 74% | 2.01 |
| Example 17 | 14.80% | 2.50 | 4.0 | 0.86 | 67% | 2.50 |
| Example 18 | | | | 1.71 | 76% | 2.49 |

Examples 19-24

Under a nitrogen atmosphere, spent TBHP-Al$_2$C IL containing 6.82% wt conjunct polymer was added to a flask equipped with a stir bar, followed by the required amount of anhydrous nC$_8$ to obtain a 0.86 vol ratio of nC$_8$ to IL, which was kept constant as shown in Table 4. The appropriate amount of triethylsilane was added to obtain the indicated ratio of triethylsilane to conjunct polymer. Stirring was initiated and continued for 15 minutes at the temperature designated in Table 4. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The % wt CP removal ranged from 25% to 80%. The results are shown in Table 4.

TABLE 4

Impact of reaction temperature on % CP Removal. Experiments conducted in nC$_8$ for 15 minutes.

| Experiment | % CP in IL | TES:CP mol ratio added | g IL | Solvent:IL vol ratio | Temp ° C. | % CP Removed | TESi:CP mol ratio converted |
|---|---|---|---|---|---|---|---|
| Example 19 | 6.82% | 1.33 | 14.0 | 0.86 | 25 | 25% | 1.33 |
| Example 20 | | | | | 80 | 42% | 1.38 |
| Example 21 | | 1.77 | 14.0 | | 25 | 37% | 1.54 |
| Example 22 | | | | | 80 | 22% | 1.87 |
| Example 23 | | 2.27 | 14.0 | | 25 | 81% | 2.28 |
| Example 24 | | | 16.0 | | 60 | 82% | 2.27 |

Examples 25-28

Under a nitrogen atmosphere, spent TBHP-Al$_2$Cl$_7$ IL containing 6.82% wt conjunct polymer was added to a glass vial equipped with a stir bar, followed by the required amount of anhydrous nC$_8$ to obtain a 0.86 vol ratio of nC$_8$ to IL, which was kept constant as shown in Table 5. The appropriate amount of triethylsilane was added to obtain a ratio of triethylsilane to conjunct polymer of 2.03. Stirring was initiated and continued for the specified amount of time as indicated in Table 5, at room temperature. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The % wt CP removal ranged from 49% to 76%. The results are shown in Table 5.

Examples 29-32

Under a nitrogen atmosphere, spent TBHP-Al$_2$Cl$_7$ IL containing 10.42% wt conjunct polymer was added to a glass vial equipped with a stir bar, followed by the required amount of anhydrous nC$_8$ to obtain a 0.86 vol ratio of nC$_8$ to IL, which was kept constant as shown in Table 5. The appropriate amount of triethylsilane was added to obtain a ratio of triethylsilane to conjunct polymer of 2.03. Stirring was initiated and continued for the specified amount of time as indicated in Table 5, at room temperature. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The % wt CP removal ranged from 55% to 80%. The results are shown in Table 5.

Examples 33-38

Figure 3:
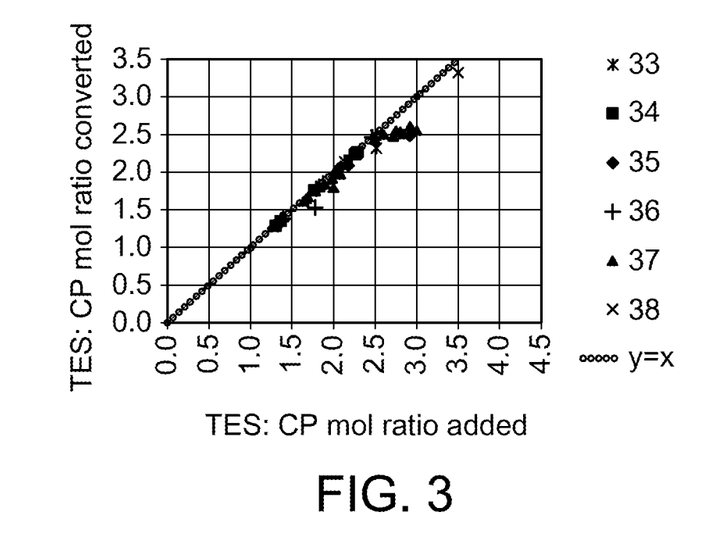
FIG. 3 is a graph showing the molar ratio of triethylsilane to conjunct polymer added as a function of the molar ratio of triethylsilane to conjunct polymer converted.

FIG. 3 is a graph showing the TESi:CP mol ratio converted as a function of the TESi:CP mol ratio added. For ionic liquids containing conjunct polymer in the range of 0-10%, approximately 2.5 molar equivalents of TESi-H are consumed relative to CP. When excess TESi-H was added to these ionic liquids, the TESi-H was not consumed by secondary reactions and could be recovered in the hydrocarbon phase and recycled back to the regenerator. For batches of ionic liquid containing up to 15% CP, the amount of TESi-H consumed per mole of CP increases to 3.5 molar equivalents.

| Example | Composition - wt % CP |
|---|---|
| 33 | 10.99% |
| 34 | 3.04% |
| 35 | 6.82% |
| 36 | 6.82% |
| 37 | 10.42% |
| 38 | 14.80% |

Examples 39-44

Figure 4:
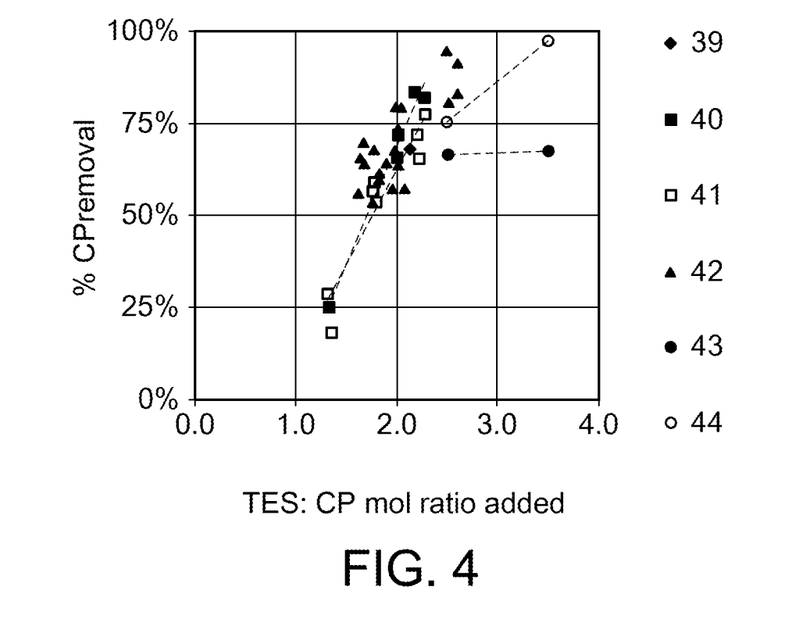
FIG. 4 is a graph showing molar ratio of triethylsilane to conjunct polymer as a function of the percentage of conjunct polymer removal.

FIG. 4 is a graph showing experiments where more than 95% of the TESi-H was converted. It shows the correlation of CP removal relative to the amount of TESi-H added. In general, the greatest amount of CP can be removed when sufficient amount of TESi-H has been added. For ionic liquids containing up to 10% CP, 2.5 mole equivalents are needed to achieve more than 80% CP removal. For ionic liquids containing up to 15% CP, 3.5 mole equivalents were needed to achieve more than 90% CP removal.

TABLE 5

Impact of reaction time on % CP removal. Experiments conducted at 25° C. in nC$_8$ with a solvent to IL volume ratio of 0.86.

| Experiment | % CP in IL | TES:CP mol ratio added | g IL | Residence Time (min) | % CP Removed | TESi:CP mol ratio converted |
|---|---|---|---|---|---|---|
| Example 25 | 6.82% | 2.03 | 7.0 | 0.25 | 49% | 0.70 |
| Example 26 | | | 7.0 | 1 | 64% | 1.63 |
| Example 27 | | | 2.5 | 3 | 76% | 1.99 |
| Example 28 | | | 4.0 | 13 | 72% | 2.01 |
| Example 29 | 10.42% | | 4.0 | 1 | 55% | 1.46 |
| Example 30 | | | 4.0 | 3 | 63% | 1.79 |
| Example 31 | | | 4.0 | 7 | 80% | 2.04 |
| Example 32 | | | 4.0 | 11 | 80% | 2.00 |

| Example | Composition - wt % CP, solvent:IL (vol) |
|---|---|
| 39 | 10.99% CP, 0.45 |
| 40 | 6.82% CP, 0.86 |
| 41 | 6.82% CP, 1.5 |
| 42 | 10.42% CP, 0.86 |
| 43 | 14.8% CP, 0.86 |
| 44 | 14.8% CP, 1.7 |

Example 45

Reduction of Chlorotriethyl silane with LiH

LiH (0.8 g; 0.1 mol) and anhydrous THF solvent (44 g; 0.616 mol) were heated with stirring to 60° C. in the drybox. Commercial grade chlorotriethylsilane (7.54 g; 0.05 mol) was added drop-wise over a span of about 15 minutes. Heating was stopped, but the reaction mixture was allowed to continue stirring at room temperature overnight. The next morning, stirring was stopped, and a liquid aliquot was analyzed by GC after filtration. Conversion of TES-Cl to TES was found to be about 82%. The reaction mixture was heated again for another 2 hours and allowed to stir overnight at room temperature. GC analysis the next morning confirmed complete conversion.

Example 46

Reduction of Chlorotriethyl Silane with NaAlH$_4$

NaAlH$_4$ (1.43 g; 0.0265 mol), tributylhexylphosphonium chloride (0.21 g; 0.00065 mol), and toluene (265 mL) were heated with stirring to 65° C. in the glovebox. Commercial grade chlorotriethylsilane (2.0 g; 0.013 mol) was added drop-wise over the span of about 10 minutes. After 1 hour, heating was stopped, but the reaction mixture was allowed to continue stirring at room temperature overnight. The next morning, stirring was stopped, and a liquid aliquot was analyzed by GC. Conversion of TES-Cl to TES-H was found to be only about 24%. The reaction mixture was heated again for another 4 hours and allowed to stir over the weekend at room temperature. GC analysis then confirmed complete conversion.

Example 47

Reduction of Chlorotriethylsilane in the Presence of CP and Solvent with LiH

In the glovebox, 18 g of spent IL (6.16% wt CP), triethylsilane (0.645 g; 0.0055 mol), and 4 g of nC$_6$ were contacted at room temperature for 15 minutes. An aliquot of the product solution was analyzed by GC showing 69% conversion of TES to TES-Cl. To the organic phase from the reaction above was added anhydrous THF (4.89 g; 0.068 mol) and LiH (0.09 g; 0.011 mol). The reaction stirred at room temperature overnight. The next morning GC analysis showed that only 15% of the TES-Cl had converted to TES. The reaction mixture was heated to 60° C. for 3.5 hours after which complete conversion to TES was obtained.

Example 48

Borane

Spent ionic liquid samples were generated in a continuous alkylation process in which 2-butenes were contacted with tributylhexylphosphonium heptachloroaluminate ionic liquid in the presence of isobutane and 2-chlorobutane. Contacting took place in a stirred 300 mL autoclave stirred at 1200 rpm. The mixture was continuously transferred to a gravity separator and the IL recycled to the alkylation reactor. Flow rates and feed ratios varied over the course of the reaction which took place over several days to weeks for the various samples. At the end of each run, the heavy fraction containing ionic liquid was collected and stored under nitrogen.

Under a nitrogen atmosphere, hexane was added to spent TBHP-Al$_2$Cl$_7$ ionic liquid containing conjunct polymer followed by the addition of 9-BBN as a solution in hexane. After stirring in an autoclave for 1 hr at 70° C., the mixture was allowed to settle to separate the hexane layer and the ionic liquid layer. The hexane layer was decanted from the ionic liquid layer. The ionic liquid layer was further washed with pentane. Upon exposure to air, a white precipitate was formed which was filtered out of the hexane layer. The volatiles were removed from the hexane layer to isolate the conjunct polymer as a viscous oil (92% of the conjunct polymer was isolated). The isolated conjunct polymer is a similar molecular weight to conjunct polymer previously isolated using silane compounds. The addition of 2-chlorobutane to the ionic liquid layer restored the activity of the ionic liquid. The performance was similar to fresh ionic liquid, with a RONC of 95 for the regenerated ionic liquid and a RONC of 94 for the fresh ionic liquid, and with a butene conversion of 99% for both ionic liquids.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for regenerating at least one silyl or boryl compound comprising:
   providing an organic phase comprising conjunct polymer and the at least one silyl or boryl compound;
   chemically reducing the at least one silyl or boryl compound with a hydrogen containing compound in a silane or borane regeneration zone under regeneration conditions to form at least one regenerated silane or borane compound and a metal salt compound; and
   recovering the at least one regenerated silane or borane compound.

2. The method of claim 1 wherein the hydrogen containing compound is a metal hydride.

3. The method of claim 2 wherein the metal hydride comprises LiH, NaH, CaH$_2$, NaAlH$_4$, LiAlH$_4$, KH, NaBH$_4$, diisobutylaluminum hydride, or combinations thereof.

4. The method of claim 1 wherein the organic phase further comprises a solvent.

5. The method of claim 4 further comprising separating the solvent from the organic phase before chemically reducing the at least one silyl or boryl compound with the hydrogen containing compound.

6. The method of claim 4 further comprising separating the solvent from the organic phase after chemically reducing the at least one silyl or boryl compound with the hydrogen containing compound.

7. The method of claim 4 wherein the solvent comprises a normal paraffin, an isoparaffin, or a cyclic paraffin having up to 10 carbon atoms, an aromatic, or the at least one silane or borane compound.

8. The method of claim 1 further comprising adding a second solvent to the organic phase before chemically reducing the at least one silyl or boryl compound with the hydrogen containing compound.

9. The method of claim 8 wherein the second solvent comprises tetrahydrofuran or toluene.

10. The method of claim 1 further comprising separating at least a portion of the conjunct polymer from the organic phase before chemically reducing the at least one silyl or boryl compound with the hydrogen containing compound.

11. The method of claim 1 further comprising separating the at least one regenerated silane or borane compound from the metal salt compound before recovering the at least one regenerated silane or borane compound.

12. The method of claim 1 wherein the at least one silyl compound has the formula: $R_3SiX$, $R_2SiX_2$, $RSiX_3$, or $SiX_4$, where each R is independently selected from hydrocarbons, and each X is independently selected from halides; or wherein the at least one boryl compound has the formula $R_2BX$, where each R is independently selected from hydrocarbons or halides, or is a boron halide compound.

* * * * *